United States Patent [19]

Grandadam et al.

[11] 4,431,640
[45] Feb. 14, 1984

[54] PROCESS FOR INDUCING ANABOLIC AND ANDROGENIC ACTIVITY IN ANIMALS

[75] Inventors: Jean A. Grandadam, Saint-Maur des Fosses; Huguette Dreux, Jean G. Feutsch, Pantin, all Neuilly-sur-Seine., of France

[73] Assignee: Roussel Uclaf, Paris, France

[21] Appl. No.: 325,993

[22] Filed: Nov. 30, 1981

[30] Foreign Application Priority Data

Dec. 5, 1980 [FR] France .................................. 80 25868

[51] Int. Cl.³ ............................................. A61K 31/56
[52] U.S. Cl. ................................. 424/243; 260/397.45
[58] Field of Search .................... 260/397.45; 424/243

[56] References Cited

U.S. PATENT DOCUMENTS 3,624,110 11/1971 Hughes et al. ...................... 424/243
4,233,296 11/1980 Teutsch et al. ................... 260/239.5

*Primary Examiner*—Elbert L. Roberts
*Attorney, Agent, or Firm*—Hammond & Littell, Weissenberger and Muserlian

[57] ABSTRACT

Novel $\Delta^{4,9}$-estradienes of the formula

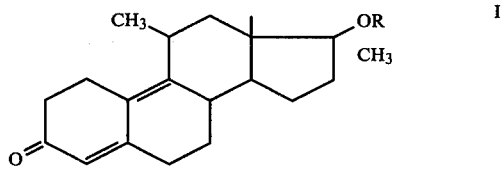

wherein R is selected from the group consisting of hydrogen, alkyl of 1 to 8 carbon atoms and acyl of an organic carboxylic acid of 1 to 18 carbon atoms having exceptional anabolic and androgenic activity and their preparation.

6 Claims, No Drawings

PROCESS FOR INDUCING ANABOLIC AND ANDROGENIC ACTIVITY IN ANIMALS

STATE OF THE ART

U.S. Pat. No. 4,233,296 describes a genus of $\Delta^{4,9}$-estradienes but the present compounds are not described or named in the patent.

OBJECTS OF THE INVENTION

It is an object of the invention to provide the novel compounds of formula I and a novel method for their preparation.

It is another object of the invention to provide novel anabolic and androgenic compositions and a novel method of inducing anabolic and androgenic activity in warm-blooded animals.

These and other objects and advantages of the invention will become obvious from the following detailed description.

THE INVENTION

The novel products of the invention are $\Delta^{4,9}$-estradienes of the formula

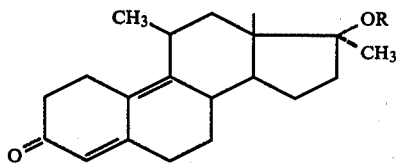

wherein R is selected from the group consisting of hydrogen, alkyl of 1 to 8 carbon atoms and acyl of an organic carboxylic acid of 1 to 18 carbon atoms.

When R is alkyl of 1 to 8 carbon atoms, it is preferably methyl, ethyl, propyl, isopropyl, butyl, tert.-butyl or isobutyl.

When R is acyl of an organic carboxylic acid, it is preferably an optionally unsaturated aliphatic or cycloaliphatic carboxylic acid such as alkanoic acids like formic acid, acetic acid, propionic acid, butyric acid, isobutyric acid or undecylic acid; hydroxy alkanoic acids such as hydroxy acetic acid; cycloalkyl carboxylic acids and cycloalkyl alkanoic acids like cyclopropylcarboxylic acid, cyclopentylcarboxylic acid, cyclohexycarboxylic acid, cyclopentylacetic acid, cyclohexylacetic acid, cyclopentylpropionic acid or cyclohexylpropionic acid; benzoic acid or phenylalkanoic acid like phenylacetic acid or phenylpropionic acid; amino acids such as diethylaminoacetic acid and aspartic acid.

The novel process of the invention for the preparation of the compounds of formula I comprises reacting a compound of the formula

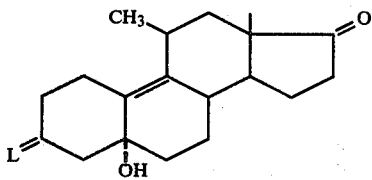

wherein L is a ketal group with a methylation agent and then with a dehydration agent capable of simultaneously removing the ketal group to obtain $11\beta,17\alpha$-dimethyl-$\Delta^{4,9}$-estradiene-$17\beta$-ol-3-one which is a compound of formul I wherein R is hydrogen which may be reacted with an etherification agent or an esterification agent to obtain a compound of formula I wherein R is alkyl of 1 to 8 carbon atoms or acyl of an organic carboxylic acid of 1 to 18 carbon atoms, respectively.

The L ketal group may be a cyclic alkylene ketal of 2 to 4 carbon atoms, preferably ethylenedioxy or propylenedioxy, or a dialkyl ketal of 1 to 4 carbon atoms such as dimethyl ketal or diethyl ketal. The methylation agent is preferably a methyl magnesium halide such as methyl magnesium bromide or chloride.

The dehydration agent capable of simultaneously freeing the ketone group is preferably a sulfonic acid resin in the acid form such as the commercial sulfonic acid resins based on polystyrene or styrene-divinylbenzene copolymers but also useful are mineral acids such as hydrochloric acid or sulfuric acid in a lower alkanol or perchloric acid in acetic acid or a sulfonic acid such as p-toluene sulfonic acid.

The esterification and the etherification of the compound of formula I wherein R is hydrogen may be effected by classical methods. For example, the etherification may be effected by reacting the sodium derivative of $11\beta,17\alpha$-dimethyl-$\Delta^{4,9}$-estradiene-$17\beta$-ol-3-one with an alkyl halide of 1 to 8 carbon atoms and the esterification may be effected by reacting $11\beta,17\alpha$-dimethyl-$\Delta^{4,9}$-estradiene-$17\beta$-ol-3-one with a functional acid derivative such as the acid chloride or acid anhydride.

In a modification of the process of the invention, a 3-ketal of $11\beta$-methyl-$\Delta^9$-estrene-$5\alpha$-ol-3,17-dione is reacted with a compound of the formula CH$_3$-M wherein M is metallic cation or -MgX$_1$ and X$_1$ is a halogen to form the 3-ketal of $11\beta,17\alpha$-dimethyl-$\Delta^9$-estrene-$5\alpha,17\beta$-diol-3-one, reacting the latter with an alkyl halide to form the 3-ketal of $5\alpha,17\beta$-dialkoxy-$11\beta,17\alpha$-dimethyl-$\Delta^9$-estrene-3-one and reacting the latter with H$_3$O$^+$ to obtain $11\beta,17\alpha$-dimethyl-$17\beta$-alkoxy-$\Delta^{4,9}$-estradiene-3-one.

The starting compounds of formula II may be prepared by the process of U.S. Pat. No. 4,233,296.

The anabolic and androgenic compositions of the invention are comprised of an anabolically and androgenically effective amount of at least one compound of formula I and an inert pharmaceutical carrier or excipient. The compositions may be in the form of tablets, dragees, cachets, capsules, granules, syrups, emulsions, suppositories and injectable solutions or suspensions. Especially preferred is the compound of formula I wherein R is hydrogen.

The compositions have an unexpected, very important exceptional anabolic activity and androgenic activity as compared to the products described in the examples of U.S. Pat. No. 4,233,296 as will be seen in the pharmacological data presented herein. The compositions are useful in the treatment of andropause, of adisopogenital syndrome, of functional metrorragia, of fibroma and of endometriosis as well as asthenia, osteroporosis, senescenes and metabolic perturbations after prolonged treatment with corticotheraphy.

Examples of excipients are talc, arabic gum, lactose, starch, magnesium stearate, cacao butter, aqueous or non-aqueous vehicles, fatty bodies of animal or vegetable origin, paraffinic derivatives, glycols, diverse wetting agents, dispersants, or emulsifiers and preservatives.

The method of inducing anabolic and androgenic activity in warm-blooded animals, including humans, comprises administering to warm-blooded animals an anabolically and androgenically effective amount of at least one compound of formula I, especially that wherein R is hydrogen. The compounds may be administered orally, rectally, percutaneously or intraveinously and the usual daily dose is 0.002 to 0.04 mg/kg depending on the method of administration and the specific compound.

The compositions are also useful in veterinary medicine to increase the general organic resistance to all sorts of aggressions, to combat the retarding of growth, thinness, general organic troubles due to a state of senescence and also to combat on a secondarily against infections, parasitic and nutritional maladies and to promote the weight of the animal to a higher level. The veterinary compositions are useful for increasing the weight of animals such as bovines, pigs, sheeps and fowl.

The veterinary compositions are preferably administrated in the form of an implant under the skin, preferably at the base of the ear or in the neck or the fessier muscles. The implants are preferably placed 20 days to 4 months before slaughter, most preferably 1 to 3 months. The dosage used to obtain good results on calves varies from 50 to 400 mg in the form of one or more percutaneous treatments and to obtain excellent results with calves, two percutaneous treatments spaced about 5 to 10 days apart using 150 to 250 mg of the active compound have been used. The product of Example 1 has been administered twice at a dose of 200 mg a week apart, for example.

When the compositions of the invention are used to promote the increase in weight of animals, they may be additives for the animal feed and may be associated with a nutritive mixture adapted to the animal feed. The nutritive mixture may contain cereals, sugars and grasses, soja press cake, arachide and tournesol, meal of animal origin such as fish meal, synthetic amino acids, mineral salts, vitamins and antioxidants.

In the following examples there are described several preferred embodiments to illustrate the invention. However, it should be understood that the invention is not intended to be limited to the specific embodiments.

EXAMPLE 1

11$\beta$,17$\alpha$-dimethyl-$\Delta^{4,9}$-estradiene-17$\beta$-ol-3-one

An ether solution of 2.25 M of methyl magnesium bromide was added with stirring under an inert atmosphere at a regular rate over 40 minutes to a solution of 100 g of 3,3-dimethoxy-11$\beta$-methyl-$\Delta^{9(10)}$-estrene-5$\alpha$-ol-17-one [prepared by process of Belgium Pat. No. 862,868] in 700 ml of dichloroethane while allowing the temperature to rise. The mixture was stirred at 40° C. under an inert atmosphere for 105 minutes and was then cooled to 20° C. and poured into 600 ml of iced water and 400 g of ammonium chloride. The mixture was stirred for 10 minutes and the decanted aqueous phase was extracted with chloroform. The organic extract was washed with water, dried and evaporated to dryness under reduced pressure and the residue was subjected to entrainment with 100 ml of 95% ethanol. The product was dissolved in 836 ml of ethanol and 83.6 g of Redex CF resin were added to the solution. The mixture was refluxed for 3 hours and was filtered at 65° C. The filtrate was evaporated to dryness and the product was entrained with acetone. The oily residue was taken up in acetone and the mixture was iced at −10° C. and was vacuum filtered. The product was rinsed at −20° C. with acetone and the 25 g of raw product was crystallized from ethyl acetate to obtain 11$\beta$,17$\alpha$-dimethyl-$\Delta^{4,9}$-estradiene-17$\beta$-ol-3-one melting at 157.5° C. and having a specific rotation of $[\alpha]_D^{20} = -141.5°$ (c=1% in chloroform).

EXAMPLE 2

The androgenic activity of the compound of Example 1 and 11$\beta$-propyl-17$\alpha$-methyl-$\Delta^{4,9}$-estradiene-17$\beta$-ol-3-one (compound A) were compared by the hormonal receptor method of Raynaud et al [J. Ster. Biochem., Vol. 6 (1975), p. 615–622]. The prostate was removed from male rats castrated 24 hours earlier and it was homogenized in a buffered 10 mmole tromethamine solution containing 0.25 M of saccharose and a pH of 7.4 with hydrochloric acid. The homogenate was centrifuged at 105,000 g for one hour and the liquid surnageant or "cytosol" was adjusted to obtain a 1/5 (weight/volume) dilution.

The cytosol with a fixed concentration of tritied 17$\beta$-methyl-$\Delta^{4,9,11}$-estratriene-17$\beta$-ol-3-one designated as tritied R was incubated at 0° C. for 2 hours in the presence or absence of an increasing concentration of the same cold product designated as cold R, of testosterone or a test compound. The radioactivity of tritied product was determined after about 2 hours in the receptor by the technique of carbon-dextran (1.25%–0.625%) absorption. The curves representing the percentage of tritied R as a function of the log of the concentration of the cold R product or testosterone or the test compound and the $I_{50}$ straight line parallel to the axis of the abcisses and ordinate $$\frac{B}{T} = \frac{B/T\,\text{max.} + B/T\,\text{min.}}{2}$$

were traced. B/T max. is the percentage of tied tritied R product when the compound is not added. B/T min. is the percentage of tied tritied product R when the maximum amount of cold product R is added. The intersections of this $I_{50}$ straight line and the curves permit one to determine the values of CX (concentration of test product which inhibits by 50% the fixation of tritied product R) and CT (concentration of cold testosterone which inhibits by =% the fixation of tritied product R). The relative affinity of the test product or ARL was determined using the formula $$ARL = 100 \times \frac{CT}{CX}$$

The ARL values obtained were 100 for testosterone, 90 for the compound of Example 1 and 22 for product A. This means that the product of Example 1 has a much greater affinity for androgen receptor than prior art product A.

EXAMPLE 3

This test was effected with groups of calves of the FFPN race and all groups received the same amount of feed. The control group were untreated and the other group received percutaneously on day J and J+7 200 mg of the compound of Example 1. The weights of the animals were determined 7 days before the treatment (J−7), on the day of treatment (J), on the day of the second treatment (J+7) and one week after the second treatment (J+14) and the results are reported in the following Table.

TABLE

| On Day | Average weight of calves in kg | |
|---|---|---|
| | Control | Treated |
| J − 7 | 45.23 | 45.50 |
| J | 52.10 | 52.30 |
| J + 7 | 59.42 | 60.47 |
| J + 14 | 67.78 | 70.67 |
| Average weight gain | 15.68 | 18.37 |

In the 7 days after the test which is J 14 to J 21, the control calves showed an average weight gain of 6.28 kg while the treated calves showed an average weight gain of 8.63 kg in the same period. This data means that the product of Example 1 permits a very clear increase in the average weight gain of the calves.

EXAMPLE 4

An implant was prepared containing 140 mg of the product of Example 1 and sufficient excipient for an implant. Also prepared was a pomade containing 40 mg per g of the product of Example 1.

Various modifications of the products and method of the invention may be made without departing from the spirit or scope thereof and it is to be understood that the invention is intended to be limited only as defined in the appended claims.

What we claim:

1. A method of inducing anabolic and androgenic activity in warm-blooded animals comprising administering to warm-blooded animals to anabolically and androgenically effective amount of at least one compound of the formula

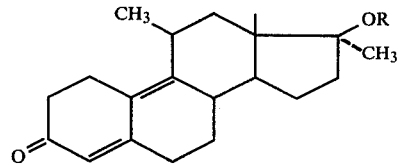

wherein R is selected from the group consisting of hydrogen, alkyl of 1 to 8 carbon atoms and acyl of an organic carboxylic acid of 1 to 18 carbon atoms.

2. The method of claim 1 wherein R is hydrogen.

3. The method of increasing the weight of slaughter animals comprising administering to immature slaughter animals an anabolically effective amount of at least one compound of the formula

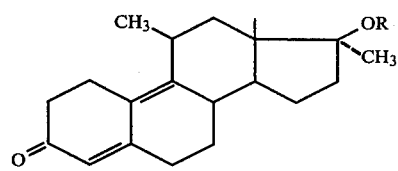

wherein R is selected from the group consisting of hydrogen, alkyl of 1 to 8 carbon atoms and acyl of an organic carboxylic acid of 1 to 18 carbon atoms.

4. The method of claim 3 wherein R is hydrogen.

5. The method of claim 3 wherein the compound is administered as a percutaneous implant.

6. The method of claim 3 wherein the compound is administered orally by addition to the animals feed.

* * * * *